United States Patent [19]
Getz

[11] Patent Number: 5,678,251
[45] Date of Patent: Oct. 21, 1997

[54] SCENTED UNDERGARMENTS

[75] Inventor: Matthew S. Getz, Stamford, Conn.

[73] Assignee: Scent-Sation, Inc., N.Y.

[21] Appl. No.: 688,367

[22] Filed: Jul. 30, 1996

[51] Int. Cl.⁶ .................................................. A41B 9/04
[52] U.S. Cl. ........................................ 2/406; 2/408
[58] Field of Search ........................... 2/406, 400, 408,
2/1, 244, 170, 247, 250; 512/4; 223/86

[56] References Cited

U.S. PATENT DOCUMENTS

| | | |
|---|---|---|
| 2,124,396 | 7/1938 | Frank. |
| 2,256,917 | 9/1941 | Wolwode et al.. |
| 2,626,833 | 1/1953 | Valentine. |
| 2,719,976 | 10/1955 | Sussman ........................... 2/408 |
| 2,806,315 | 9/1957 | Kalensky. |
| 3,185,394 | 5/1965 | Farrell. |
| 3,424,162 | 1/1969 | Parravicini. |
| 3,688,985 | 9/1972 | Engel ............................. 239/54 |
| 4,155,123 | 5/1979 | Popper. |
| 4,244,059 | 1/1981 | Pflaumer. |
| 4,277,024 | 7/1981 | Spector. |
| 4,387,849 | 6/1983 | Van Lovern et al.. |
| 4,465,232 | 8/1984 | Field. |
| 4,552,693 | 11/1985 | Hussain et al. ................. 512/4 |
| 4,605,165 | 8/1986 | Van Loveren et al.. |
| 4,614,299 | 9/1986 | Van Loveren et al.. |
| 4,734,278 | 3/1988 | Pougalan et al. ............... 512/4 |
| 4,842,761 | 6/1989 | Rutherfold. |
| 4,874,129 | 10/1989 | DiSapio et al.. |
| 4,928,323 | 5/1990 | Nathan. |
| 5,067,178 | 11/1991 | Katchka. |
| 5,093,935 | 3/1992 | Countee. |
| 5,172,430 | 12/1992 | Lerma-Solis. |
| 5,399,404 | 3/1995 | Laughlin et al.. |

OTHER PUBLICATIONS

Brochure entitled "POLYIFF" by International Flavors and Fragrances, Inc.

Primary Examiner—Gloria Hale
Attorney, Agent, or Firm—Abelman, Frayne & Schwab

[57] ABSTRACT

The invention relates to the emplacement of a water-insoluble, polymeric scent-emitting tablet in a fabric chamber formed by a medallion stitched to the surface of women's intimate apparel to provide a long-lasting fragrance despite repeated laundering.

20 Claims, 1 Drawing Sheet

SCENTED UNDERGARMENTS

BACKGROUND OF THE INVENTION

1. Field of the Invention

The present invention relates to a female undergarment or item of intimate apparel and, more particularly, to a female undergarment provided with a means for securely containing a scent-emitting element.

2. Background Art

Throughout recorded history, beginning with the bible and continuing to the present, women have always been portrayed as employing fragrances on their person to enhance their self-image, as a means of attracting male attention and to allay any concerns associated with personal hygiene, either of a real or perceived nature. The development of the perfume and fragrance industry from a cottage industry to multinational corporations manufacturing and selling on a global basis has successfully capitalized on the allure and mystique associated with fragrances. The olfactory sense has proven an extremely potent tool in the marketing of a vast variety of goods to which scents or fragrances have been imparted.

In the marketing of women's intimate apparel, such as panties, brassieres, slips, panty girdles, etc., marketers have principally sought to appeal to the visual and tactile senses by creating designs and employing fabrics which appeal to womens' sense of beauty, as well as comfort.

At the present time, while the design of female intimate apparel to provide support, comfort and allure is at its aesthetic zenith, by appealing to women's visual and tactile senses, no designs have been developed which would also provide an appeal to the olfactory sense. The development of female intimate apparel possessed of a long-lasting fragrance, either a subtle or bold scent, or a blend between the bold and the subtle, would provide women with an enhanced sense of emotional well-being, as well as imparting a pleasing fragrance to their person.

Accordingly, it is an object of the present invention to provide women's intimate apparel, such as panties, brassieres, slips, etc., with a long-lasting, fragrance-emitting element which will appeal to their olfactory sense.

It is another object of the present invention to provide women's intimate apparel with a long-lasting scent or fragrance which will not dissipate despite repeated laundering.

It is still another object of the present invention to provide a long-lasting scent to women's intimate apparel which will not acquire or be contaminated with ambient odors during wearing or laundering.

It is yet another object of the present invention to provide a scent emitting device which is contained within an hidden retaining means secured to women's intimate apparel and which cannot be dislodged.

SUMMARY OF THE INVENTION

By virtue of the present invention women's intimate apparel can now be provided with an unobtrusive, hidden, long-lasting fragrance- or scent-emitting element, which is securely retained in the garment, and which will provide a continuous scent, without solubilizing upon repeated washing or laundering and in addition, will not be contaminated by ambient odors present in the environment during wear of the apparel or in the detergent employed during in the laundering thereof.

A female undergarment such as, for example, panties, brassieres, slips, etc., which comprises a medallion securely attached to a surface of the undergarment defining a closed containment element or chamber, a water-insoluble, scent-emitting element disposed within the confines of said chamber whereby said scent-emitting element will not solubilize during laundering while continuously releasing a pleasing aromatic scent.

Features of the present invention which are believed to be novel and unobvious are particularly pointed out and distinctly claimed in that portion of the specification which follows. The inventions, however, together with further objects and advantages thereof, may best be appreciated by reference to the following detailed description when taken in conjunction with the drawings described hereinafter.

DETAILED DESCRIPTION OF THE INVENTION

Figure 1:
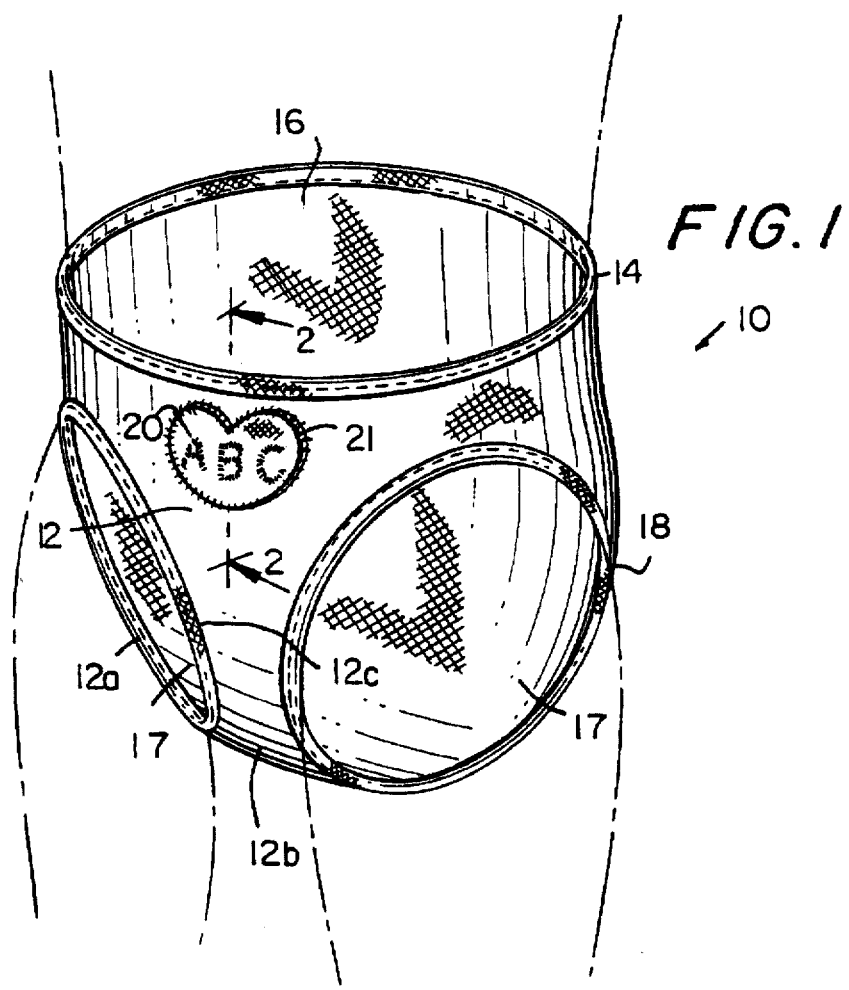
FIG. 1 is a perspective view of a pair of women's panties in accordance with the present invention.
Figure 2:
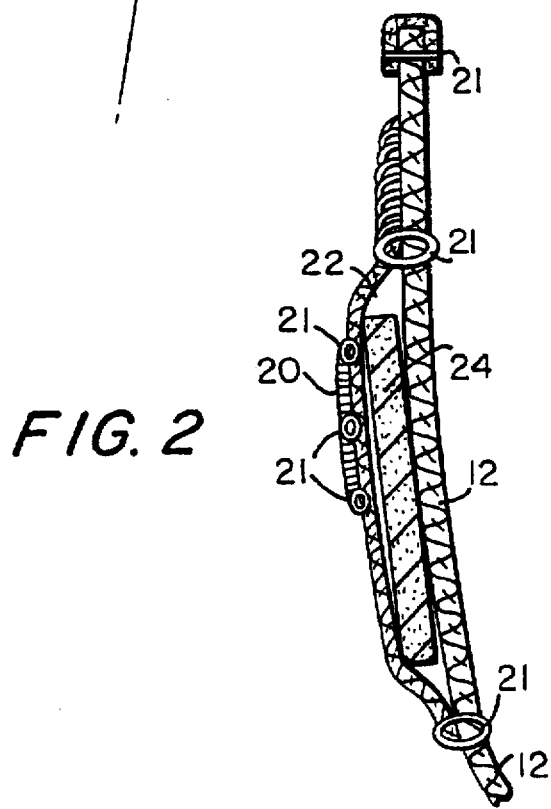
FIG. 2 is a cross sectional view along the line 2—2 of FIG. 1 of the scent emitting element in accordance with the present invention.

Referring now to FIGS. 1 and 2 of the drawings, wherein like numbers refer to like parts, a pair of women's panties 10 is depicted having a front panel 12, said front panel being joined to a rear panel 12a at the side edges thereof and a crotch panel 12b joined to panels 12 and 12a at the bottom edges thereof. A waistband 14, which is preferably of an elastic material, is provided which is joined to panels 12 and 12a at the top edges thereof and defines a waist opening 16. The panties further include leg openings 17, which may be defined by elastic tapes 18.

The panties 10 can be made entirely of a synthetic material, such as, polyester or nylon, or they can be made entirely of a fabric constructed of natural fibers, such as, for example, cotton. Alternatively, the panties can be a blend, in suitable proportions, of a synthetic material and a naturally occurring material, or two synthetic materials. Particularly preferred in accordance with the present invention are panties made of 95% nylon and 5% LYCRA® Spandex fabric.

The inner surface of crotch panel 12b includes a superimposed cotton knit panel 12c, which is sewn in place. The superimposed cotton knit panel 12c, overlies crotch panel 12b, to provide an absorbent surface in an area where sweat and moisture tend to accumulate.

A medallion 20, preferably with identifying indicia thereon, such as, for example, an embroidered trademark or tradename 21, is permanently secured to the outer surface of front panel 12, specifically centrally of said front panel 12 and proximate elastic waistband 14. It is preferred that the medallion 20 be made of 95% nylon and 5% LYCRA® Spandex fabric, the same material which is employed in the panties 10, per se, and that the backing material of the medallion 20 be made of tricot, which is porous in nature.

The medallion 20, and that portion of the outer surface of front panel 12 to which the medallion is secured, as by stitching 21, serves to form a secure, sealed containment element or chamber 22. In accordance with the present invention, after the medallion 20 has been sewn or stitched closed on three sides thereof, a fragrance- or scent-emitting, water-insoluble plastic tablet 24 is emplaced in containment element 22 and the remaining open side, i.e., the fourth side, is then stitched to completely close the containment element 22 and seal tablet 24 therein. The sealed-off tablet 24 can be seen in phantom by reference to FIG. 1 and in cross-section in FIG. 2.

The tablet 24 is depicted as being generally heart-shaped in configuration which conforms to the configuration of the medallion 20. Alternatively, the containment element 22 can be formed on an inner surface of the front panel 12 or the rear panel 12a and worn adjacent to the wearer's skin. In still another embodiment of the present invention, the containment element 22 can be secured to the outer surface of rear panel 12a. It is preferred, however, to locate the medallion 20 and the emplaced tablet 24 centrally of front panel 12 and proximate waistband 14 since such placement provides a dual benefit, namely, optimum fragrance dispersion and uniform stretchability of the elastic waistband without distortion.

Tablet 24 can also be circular, elliptical, oval, rectangular, etc. or, in fact, any convenient configuration which is substantially similar to the configuration of the containment chamber 22. Naturally, the tablet 24 should be somewhat smaller than chamber 22 so that it can be readily emplaced or sandwiched into chamber 22, prior to medallion 20 being stitched closed, to insure complete enclosure of the tablet 24 within chamber 22 in order to prevent loss of the tablet during wear or laundering and to preclude access thereto.

The tablet 24 is formed by extruding a water-insoluble, thermoplastic resin, into which have been blended fragrance-containing beads. These fragrance-containing beads are uniform dispersions of natural or synthetic essential oils, or mixtures of both, in a solid concentrate, for example, a polymeric matrix. During melt processing of the thermoplastic resin, the fragrance-containing polymeric beads are added to the melt. By this means, the fragrance oils, which are highly volatile are protected, and will not evaporate at the temperatures experienced in the extruder during melt processing.

The blending of the fragrance-containing polymeric beads with the thermoplastic water-insoluble resin is best accomplished in the feed section of the extruder. This aids in achieving a uniform fragrance throughout the product and over the entire run. It is preferred to employ from about 15% to about 30%, by weight, of the thermoplastic water-insoluble resin and from about 70% to about 85%, by weight, of the fragrance-containing polymeric beads in order to yield a fragrance-emitting pellet 24 having optimum fragrance characteristics and optimum physical properties. These weight percentages can be varied to yield a more subtle scent or a stronger scent, with a percentage of about 20% unscented to about 80% scented being especially preferred.

The water-insoluble thermoplastic base resin for use in the practice of the present invention includes low density and high density polyethylene, polypropylene and polyvinyl chloride, as well as other water-insoluble resins. It is preferred to employ polyethylene, with low density polyethylene being especially preferred.

It is also advantageous from a variety of standpoints, particularly so from the standpoint of processing compatibility with the base resin system, that the polymeric beads containing the fragrance also be low or high density polyethylene, polypropylene, or polyvinyl chloride. Again, polyethylene is preferred, with low density polyethylene being especially preferred.

It has been found particularly advantageous in the practice of the present invention to employ fragrance-containing polyethylene beads which are manufactured by International Flavors and Fragrances, Inc. of Hazlett, N.J. which are known by the trademark, POLYIFF. Exemplary of the fragrances which can be incorporated in the polymeric beads are French Vanilla, Romantic Rose, Cocoa Butter, Midnight Bouquet, etc.

In addition, during the extrusion blending operation, it is preferred to add coloring agents so that the ultimately extruded fragrance-emitting tablet will be the same color as the medallion and also the same color as the panties in order to conceal or mask the visibility of the tablet during wear. Exemplary colors which are used and which are coordinated and keyed also to the time of day or evening and the type of outer garments and accessories which are worn during those periods of time are rose, ivory, taupe and black.

Ultimately, an extruded, fragrance-emitting, water-insoluble polymeric tablet is extruded, having microscopic holes through which the fragrance diffuses via a time-release or scent-metering mechanism. The scent should possess a pleasant aromatic fragrance in order to enhance the well-being and the self-image of the wearer. A tablet-like shape is preferred since it can be readily formed by extrusion equipment and can be quite thin, for example, having a thickness of about 1/16 inches, which allows it to be completely unobtrusive when emplaced within chamber or containment element 22.

The water-insoluble nature of the polymeric tablet 24 permits it to be laundered multiple times, for example, about 52 washings, or more, without solubilizing, while still retaining its fragrant aroma without any marked dissipation in fragrance strength. In addition, the tablet 24, due to its construction, permits the scent to diffuse out, but does not pick-up the ambient orders of the detergent employed during laundering or, in fact, any of the ambient body orders occasioned during the wearing of the panties. In addition, the time-release nature of the fragrance beads in tablet 24, adverted to previously, is most advantageous since even excessive washing will not serve to diminish the aromatic fragrance emanating therefrom.

Additionally, since the tablet 24 is sandwiched or sealed-off in chamber 22 between medallion 20 and front panel 12, it does not come in contact with the wearer's skin and thus it is not a non-irritant to the skin and avoids dermatological problems.

The following example will serve to illustrate the present invention.

Four sets of four (4) pairs of womens panties made of 95% nylon and 5% LYCRA® Spandex fabric had individual scented tablets, described in detail below, emplaced within a partially open 95% nylon-5% LYCRA® Spandex fabric medallion formed on the front surface of the panties, adjacent the waistband, and the fabric medallion was then stitched closed.

The first set of four panties was ivory colored and the scented tablet, which was formed by extrusion, consisted of a blend of 20%, by weight, of unscented, low density polyethylene resin and 80%, by weight, of French Vanilla scented Polyiff® polymeric beads manufactured by International Flavors and Fragrances, Hazlett, N.J.

The second set of four panties was rose colored and the scented tablet, which was formed by extrusion, consisted of a blend of 25%, by weight, of unscented, low density polyethylene resin and 75%, by weight, of Romantic Rose scented Polyiff® polymeric beads manufactured by International Flavors and Fragrances.

The third set of four panties was black and the scented tablet, which was formed by extrusion, consisted of a blend of 25%, by weight, of unscented, low density polyethylene and 75%, by weight, of Midnight Bouquet scented polymeric beads manufactured by International Flavors and Fragrances.

The fourth set of four panties was taupe colored and the scented tablet, which was formed by extrusion, consisted of a blend of 30%, by weight, of unscented, low density polyethylene and 75%, by weight, of Cocoa Butter scented polymeric beads manufactured by International Flavors and Fragrances.

Each set of panties was then subjected to a scent longevity evaluation after laundering.

The evaluation consisted of laundering the panties in a household laundry washing machine employing the following conditions:

1. Warm Wash/Cold Rinse—Large Load
2. Permanent Press Whites
3. 10 minute Wash Cycle This was followed by drying in a household dryer on a permanent press cycle.

The panties were washed and dried with a ballast load of white terry cotton towels.

Thereafter, the panties were evaluated for fragrance retention by a panel of ten (10) persons after 10, 25 and 52 wash cycles.

The panel found that the emplaced tablet retained its fragrance even after 52 washings, of the panties, albeit with some decrease in the perceived fragrance intensity.

It is to be understood that the invention is not limited to the exact details of construction, operation or exact materials or embodiments shown or described, as obvious modifications and equivalents will be apparent to one skilled in the art, and the invention is therefore to be limited only by the scope of the appended claims.

What is claimed is:

1. A female undergarment adapted to securely retain a long-lasting, scent-emitting element, which comprises:

a fabric medallion secured to a surface of the female undergarment defining a closed containment means;

a water-insoluble, scent-emitting polymeric tablet disposed within the confines of said closed containment means which defines a sealed-off chamber to securely maintain the tablet against removal during wear or laundering;

whereby said water-insoluble, scent-emitting tablet will not solubilize even after multiple launderings while continuing to emit a scent.

2. The female undergarment according to claim 1, wherein the closed containment means defines an enclosed chamber after emplacement of the fragrance-emitting means therein.

3. The female undergarment according to claim 1, wherein the fragrance-emitting means has a configuration substantially similar to the configuration of the medallion.

4. The female undergarment according to claim 1, wherein the fabric medallion is secured by stitching to a surface of the female undergarment.

5. The female undergarment according to claim 4, wherein the undergarment is panties.

6. The female undergarment according to claim 1, wherein the scent-emitting polymeric tablet comprises a blend of a water-insoluble thermoplastic resin and scent-emitting water-insoluble polymeric beads.

7. The female undergarment according to claim 6, wherein the fragrance-emitting polymeric beads comprise from about 70% to about 85%, by weight, of the tablet.

8. The female undergarment according to claim 6, wherein the water-insoluble thermoplastic resin is selected from the group consisting of polyethylene, polypropylene and polyvinyl chloride.

9. The female undergarment according to claim 8, wherein the polyethylene is low density polyethylene.

10. The female undergarment according to claim 5, wherein the panties are selected from the group consisting of materials/fabric constructed of natural fibers, one or more synthetic fibers or mixtures thereof.

11. The female undergarment according to claim 1, wherein the scent-emitting, water-insoluble, polymeric beads comprise natural or synthetic essential oils, or mixtures thereof, dispersed in a polymeric matrix selected from polyethylene, polypropylene and polyvinyl chloride.

12. The female undergarment according to claim 11, wherein the natural or synthetic essential oil is from about 10% to about 30%, by weight, of the scent-emitting polymeric beads and the remainder is polyethylene.

13. The female undergarment according to claim 12, wherein the essential oil is about 20%, by weight, of the scent-emitting polymeric beads and the remainder is low density polyethylene.

14. The female undergarment according to claim 1, wherein the medallion is selected from the group consisting of materials/fabric constructed of natural fibers, one or more synthetic fibers, or mixtures thereof.

15. The female undergarment according to claim 14, including identifying indicia on the fabric medallion.

16. The female undergarment according to claim 15, wherein the identifying indicia are embroidered on the fabric medallion.

17. The female undergarment according to claim 5, wherein the fabric medallion is stitched to the panties on the front thereof and proximate an upper edge thereof.

18. A water-insoluble, scent-emitting polymeric element secured to a female undergarment, said scent-emitting element disposed on a front surface of said undergarment centrally thereof and proximate an edge thereof, said scent-emitting element is formulated such that it will not solubilize even after multiple launderings while still continuing to emit a scent.

19. The invention according to claim 18 wherein the scent-emitting polymeric element is confined in a closed containment means that is stitched directly thereto.

20. The invention according to claim 19 wherein the undergarment is panties.

* * * * *